US009968332B2

(12) United States Patent
Tsuruno

(10) Patent No.: US 9,968,332 B2
(45) Date of Patent: *May 15, 2018

(54) ULTRASONIC TRANSDUCER, ULTRASONIC PROBE, DIAGNOSTIC DEVICE, AND ELECTRONIC INSTRUMENT

(71) Applicant: SEIKO EPSON CORPORATION, Tokyo (JP)

(72) Inventor: Jiro Tsuruno, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/268,918

(22) Filed: Sep. 19, 2016

(65) Prior Publication Data

US 2017/0000460 A1      Jan. 5, 2017

Related U.S. Application Data

(63) Continuation of application No. 13/896,719, filed on May 17, 2013, now Pat. No. 9,474,508.

(30) Foreign Application Priority Data

May 21, 2012   (JP) .................................. 2012-115321

(51) Int. Cl.
*A61B 8/00*       (2006.01)
*B06B 1/06*       (2006.01)

(52) U.S. Cl.
CPC .......... *A61B 8/4494* (2013.01); *B06B 1/0607* (2013.01); *B06B 1/0629* (2013.01)

(58) Field of Classification Search
CPC ......... H01L 41/09; H01L 41/22; G01N 29/34; G01N 29/00; A61B 8/4455; A61B 8/44;

(Continued)

(56) References Cited

U.S. PATENT DOCUMENTS 5,761,156 A   6/1998 Reuter et al.
6,984,922 B1  1/2006 Nagahara et al.
(Continued)

FOREIGN PATENT DOCUMENTS

JP   52-150615 A   12/1977
JP   60-260848 A   12/1985
(Continued)

OTHER PUBLICATIONS

The Extended European Search Report for the corresponding European Application No. 13168240.3 dated Jan. 2, 2017.

*Primary Examiner* — Long V Le
*Assistant Examiner* — Katherine McDonald

(57) ABSTRACT

An ultrasonic transducer includes "m" first ultrasonic elements including first diaphragms, and "n" second ultrasonic elements including second diaphragms. "m" represents a number of the first ultrasonic elements and is an integer of 1 or more. Each of the first diaphragms has a first area. "n" second ultrasonic elements includes second diaphragms. Each of the "n" second diaphragms has a second area being smaller than the first area. "n" represents a number of the second ultrasonic elements and is an integer larger than "m". The "m" first ultrasonic elements are electrically connected in series in a case where "m" is an integer of 2 or more. The "n" second ultrasonic elements are electrically connected in series. B/A is within a range of 0.9 to 1.1, when a total sum of the first areas is "A" and a total sum of the second areas is "B".

10 Claims, 6 Drawing Sheets

(58) Field of Classification Search
CPC ......... G01S 7/52079; G01S 3/80; B06B 1/00; B06B 2201/20
See application file for complete search history.

(56) References Cited

U.S. PATENT DOCUMENTS

| | | |
|---|---|---|
| 7,779,696 B2 | 8/2010 | Huang |
| 2008/0013405 A1 | 1/2008 | Moon et al. |
| 2008/0089181 A1 | 4/2008 | Adachi et al. |
| 2010/0327695 A1 | 12/2010 | Goel et al. |
| 2011/0319766 A1 | 12/2011 | Tsuruno |
| 2011/0319767 A1 | 12/2011 | Tsuruno |

FOREIGN PATENT DOCUMENTS

| | | |
|---|---|---|
| JP | 2003-169800 A | 6/2003 |
| JP | 2003-339700 A | 12/2003 |
| JP | 2004-072755 A | 3/2004 |
| JP | 2005-253751 A | 9/2005 |
| JP | 2006-075425 A | 3/2006 |
| JP | 2012-005689 A | 1/2012 |
| JP | 2012-005690 A | 1/2012 |
| WO | 2009/088307 A1 | 7/2009 |

ULTRASONIC TRANSDUCER, ULTRASONIC PROBE, DIAGNOSTIC DEVICE, AND ELECTRONIC INSTRUMENT

CROSS-REFERENCE TO RELATED APPLICATIONS

This application is a continuation application of U.S. patent application Ser. No. 13/896,719, filed on May 17, 2013. This application claims priority to Japanese Patent Application No. 2012-115321 filed on May 21, 2012. The entire disclosures of U.S. patent application Ser. No. 13/896,719 and Japanese Patent Application No. 2012-115321 are expressly incorporated by reference herein.

BACKGROUND

Technical Field

The present invention relates to an ultrasonic transducer, an ultrasonic probe, a diagnostic device, and an electronic instrument.

Background Technology

An ultrasonic transducer in which a plurality of ultrasonic elements are arranged in a matrix pattern has been known. This ultrasonic transducer includes a substrate that has a plurality of openings, a supporting film that is provided on the substrate so as to cover each of the openings, and a piezoelectric element that is provided on a part of the supporting film corresponding to each of the openings. A diaphragm is constructed by the part of the supporting film corresponding to the opening which is a part coinciding with the opening of the supporting film in a planar view. The ultrasonic element is constructed by the diaphragm and the piezoelectric element provided on the diaphragm.

In this ultrasonic transducer, it has been known that two kinds of ultrasonic elements in which the areas of the diaphragms are different are provided, and are driven at different frequencies (for example, see Patent Document 1). In Patent Document 1, it is considered that the plurality of ultrasonic elements having the larger areas of the diaphragms are electrically connected in parallel with respect to each other. Likewise, it is considered that the plurality of ultrasonic elements having the smaller areas of the diaphragms are electrically connected in parallel with respect to each other.

When the two kinds of ultrasonic elements are compared, since the ultrasonic elements having the larger areas of the diaphragms have low resonance frequency, they are driven at low frequency and generate ultrasonic waves of low frequency. Also, since the ultrasonic elements having the smaller areas of the diaphragms have high resonance frequency, they are driven at high frequency and generate ultrasonic waves of high frequency. In a diagnostic device having an ultrasonic probe that uses this ultrasonic transducer, when a deep part (long distance) of a living body as a test target is diagnosed, ultrasonic waves of low frequency are used for diagnosis because ultrasonic waves of high frequency cannot reach a deep part. On the other hand, when a shallow part (short distance) of a living body is diagnosed, ultrasonic waves of high frequency are used for diagnosis so as to increase the resolution.

However, the sensitivity of an ultrasonic element becomes high as the area of the diaphragm becomes large. Therefore, the well-known ultrasonic transducer has a problem that the sensitivity of the ultrasonic elements having the smaller areas of the diaphragms is lower than that of the ultrasonic elements having the larger areas of the diaphragms. Further, due to the difference in the sensitivity, there is a problem that the magnitude of a signal output from each ultrasonic element is different, and a circuit configuration becomes complicated in order to match the magnitude of the signal.

Japanese Laid-open Patent Publication No. 2006-75425 (Patent Document 1) is an example of the related art.

SUMMARY

Problems to be Solved by the Invention

The advantage of the invention is to provide an ultrasonic transducer, an ultrasonic probe, a diagnostic device, and an electronic instrument in which the difference in the sensitivity between two kinds of ultrasonic element groups is reduced, ultrasonic waves of a plurality of frequencies can be transmitted and received, and also the circuit configuration can be simplified.

Means Used to Solve the Above-Mentioned Problems

This advantage is achieved by the invention described below. According to one aspect of the invention, an ultrasonic transducer of the invention includes "m" first ultrasonic elements and "n" second ultrasonic elements. The "m" first ultrasonic elements includes first diaphragms. The "m" first ultrasonic elements are configured and arranged to transmit and receive ultrasonic waves, where "m" represents a number of the first ultrasonic elements and is an integer of 1 or more. Each of the first diaphragms having a first area. The "n" second ultrasonic elements include second diaphragms. Each of the "n" second diaphragms has a second area being smaller than the first area. The "n" second ultrasonic elements are configured and arranged to transmit and receive the ultrasonic waves, where "n" represents a number of the second ultrasonic elements and is an integer larger than "m". The "m" first ultrasonic elements are electrically connected in series in a case where "m" is an integer of 2 or more. The "n" second ultrasonic elements are electrically connected in series. B/A is within a range of 0.9 to 1.1, when a total sum of the first areas is "A" and a total sum of the second areas is "B".

BRIEF DESCRIPTION OF THE DRAWINGS

Referring now to the attached drawings which form a part of this original disclosure.

DETAILED DESCRIPTION OF EXEMPLARY EMBODIMENTS

Hereinafter, the ultrasonic transducer, the ultrasonic probe, the diagnostic device, and the electronic instrument of the invention will be explained in detail based on a preferred embodiment shown in the attached drawings.

Embodiment of Ultrasonic Transducer and Ultrasonic Probe

Figure 1:
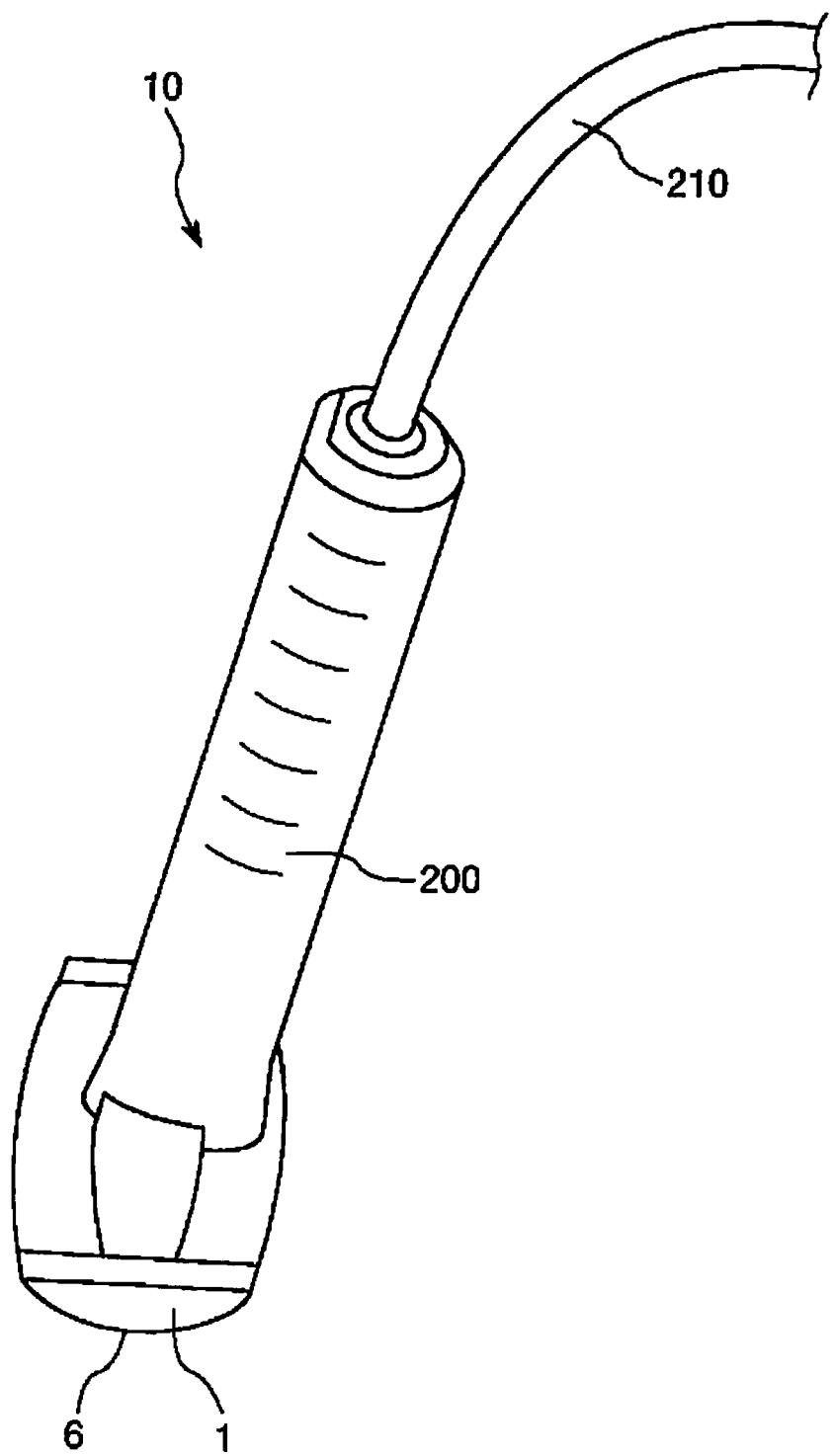
FIG. 1 is a perspective view showing an embodiment of an ultrasonic probe according to the invention.
Figure 2:
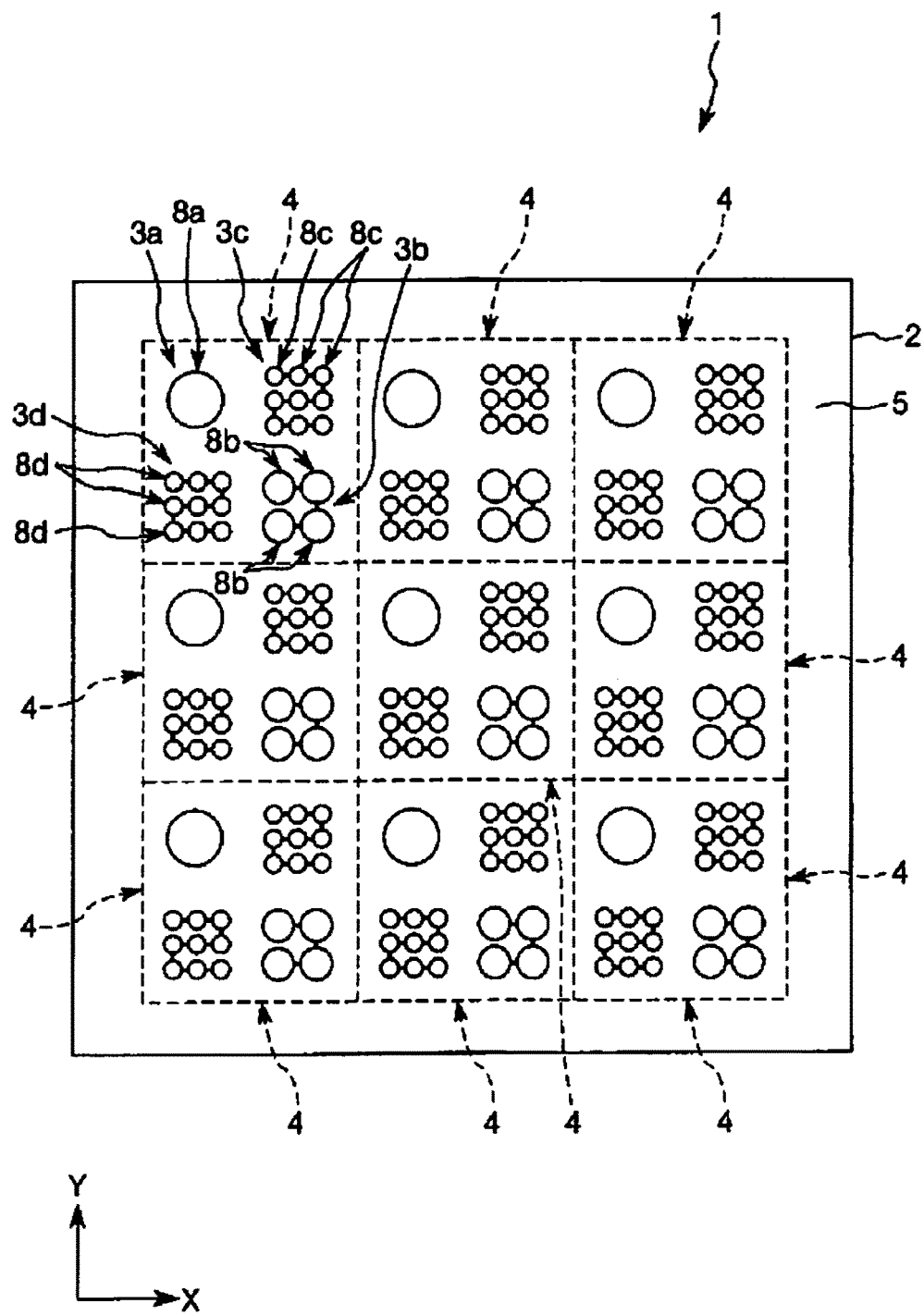
FIG. 2 is a plan view showing an ultrasonic transducer of the ultrasonic probe shown in FIG. 1.
Figure 3:
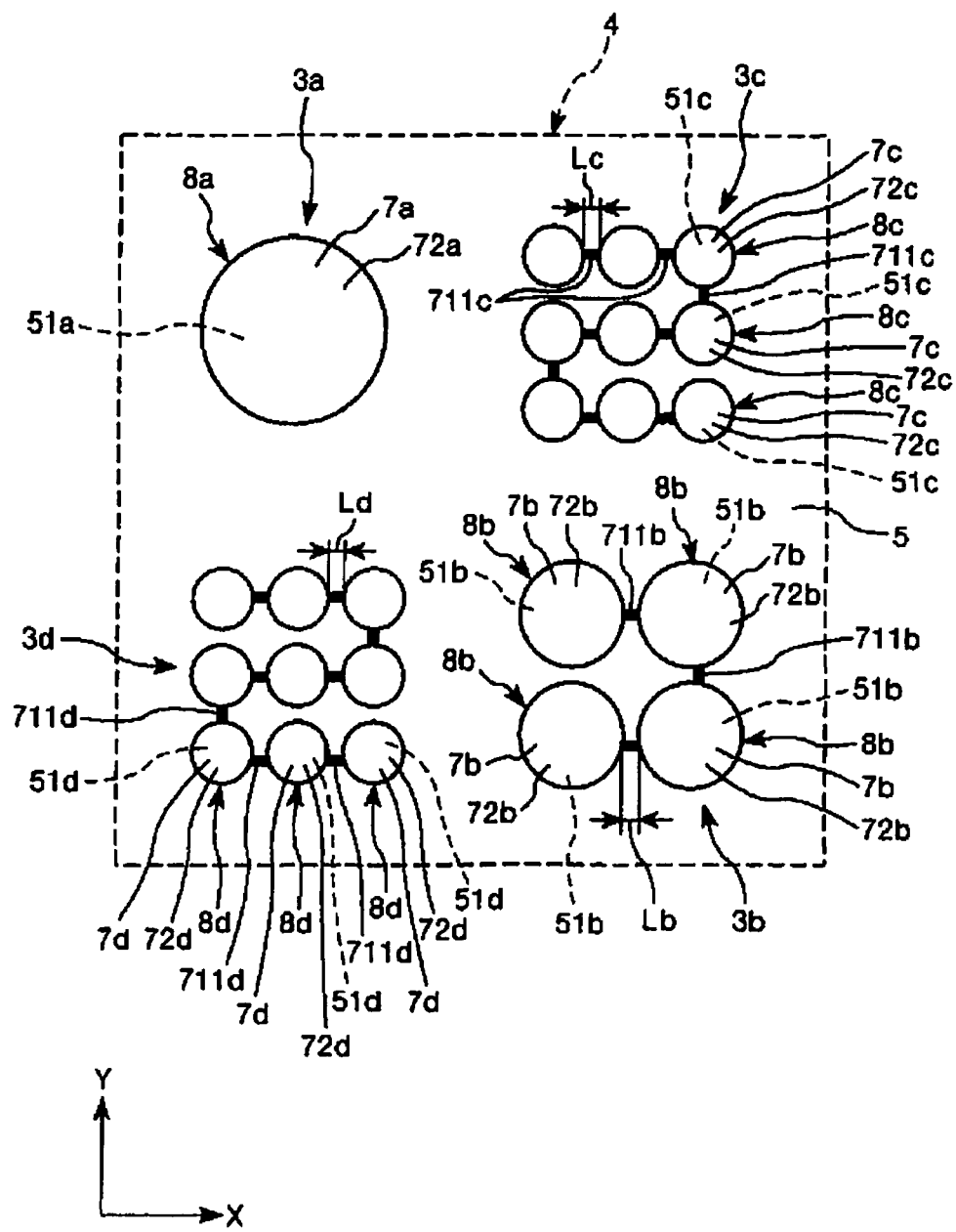
FIG. 3 is a plan view showing a cell unit of the ultrasonic transducer shown in FIG. 2.
Figure 4:
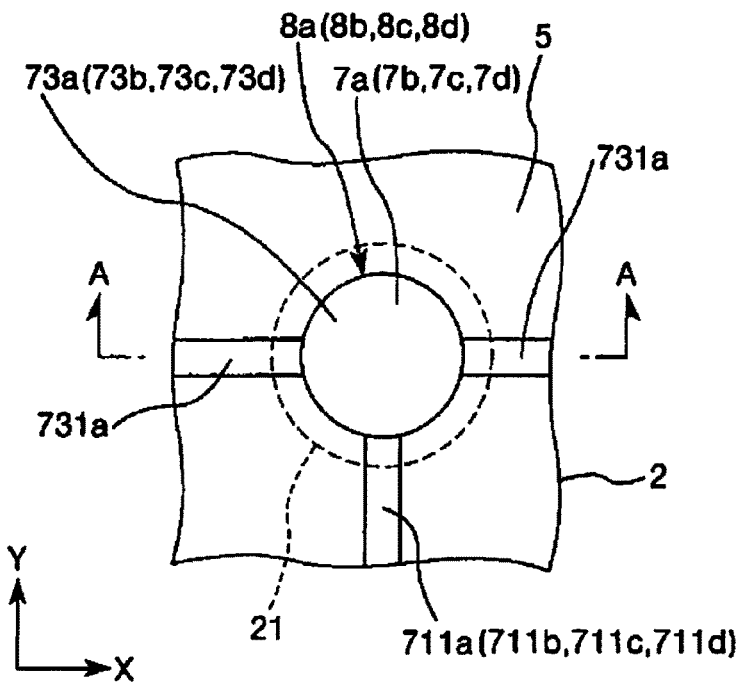
FIG. 4 is a plan view enlarging a part of the ultrasonic transducer shown in FIG. 2.
Figure 5:
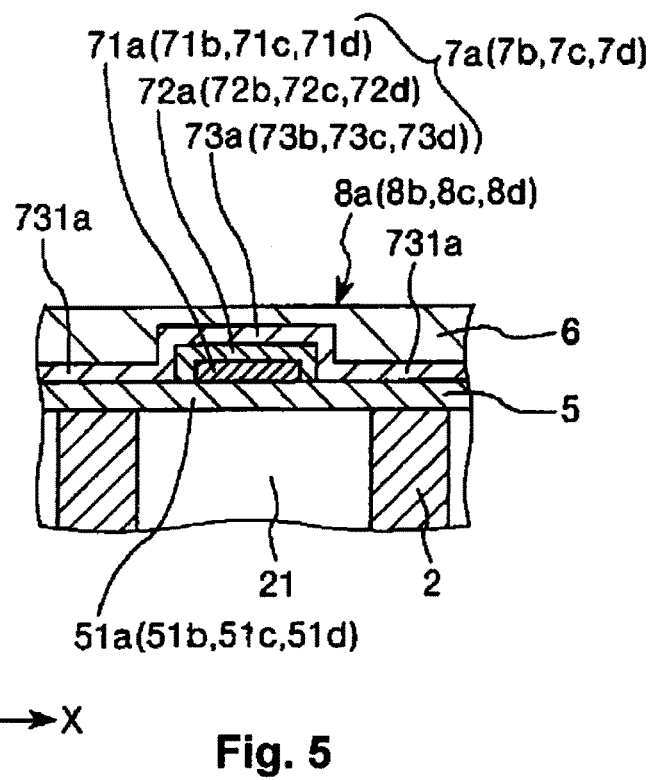
FIG. 5 is a sectional view along line A-A of FIG. 4.

FIG. 1 is a perspective view showing an embodiment of the ultrasonic probe according to the invention. FIG. 2 is a plan view showing the ultrasonic transducer of the ultrasonic probe shown in FIG. 1. FIG. 3 is a plan view showing a cell unit of the ultrasonic transducer shown in FIG. 2. FIG. 4 is a plan view enlarging a part of the ultrasonic transducer shown in FIG. 2. FIG. 5 is a sectional view along line A-A of FIG. 4.

Hereinafter, explanations will be made by describing the upper side in FIG. 2-FIG. 5 as "upper", the lower side as "lower", the right side as "right", and the left side as "left". In FIG. 2 and FIG. 3, illustrations of parts and the like of an acoustic matching section, an upper electrode, a lower electrode, a conducting wire for an upper electrode, and a conducting wire for a lower electrode are omitted, and the ultrasonic transducer is schematically illustrated. Further, in FIG. 2 and FIG. 3, the outline of the cell unit is shown by a broken line. In FIG. 4, an illustration of the acoustic matching section is omitted. Also, as shown in each drawing, an X axis and a Y axis orthogonal to each other are assumed. An X axis direction corresponds to an azimuth direction, and a Y axis direction corresponds to a slice direction.

As shown in FIG. 1, an ultrasonic probe 10 has a case 200, and an ultrasonic transducer 1 that is housed (accommodated) in the case 200. The ultrasonic transducer 1 is disposed in a tip end portion (the lower side in the drawing) of the case 200. In such a case, a substrate 2, described below, of the ultrasonic transducer 1 is fixed to the case 200 directly or with a supporting member for supporting the substrate 2. The supporting member is not shown in the drawing. The ultrasonic probe 10 can be used as an ultrasonic probe for various kinds of diagnostic devices such as a diagnostic device 100 described below.

In the present embodiment, a surface of the ultrasonic transducer 1, that is, a surface of an acoustic matching section 6 is exposed outside. The acoustic matching section 6 serves as a protective layer of the ultrasonic probe 10 and the ultrasonic transducer 1. Although the constituent material of the acoustic matching section 6 is not limited to a specific one, a material that is substantially similar to a living body with respect to the acoustic impedance, such as silicone rubber, is used. Here, it may be configured such that the surface of the acoustic matching section 6 is not exposed outside.

In the present embodiment, the ultrasonic probe 10 is a contact type sensor that is used by bringing the surface of the acoustic matching section 6 into contact with (applying to) a living body as a test target. Specifically, in conducting a test, the ultrasonic probe 10 is used by applying the surface of the acoustic matching section 6 to a living body as a test target. In such a case, when ultrasonic waves are sent out from an ultrasonic element, described below, of the ultrasonic transducer 1 toward the acoustic matching section 6, the ultrasonic waves pass through the acoustic matching section 6 and propagate through the living body. Then, the ultrasonic waves reflected on a predetermined part inside the living body pass through the acoustic matching section 6 and are input to the ultrasonic element.

Also, the ultrasonic probe 10 is electrically connected with a device main body 300 (see FIG. 6 and FIG. 7), described below, of the diagnostic device 100 through a cable 210. As shown in FIG. 2-FIG. 5, the ultrasonic transducer 1 has the substrate 2, a plurality of (nine in the configuration shown in the drawing) cell units (ultrasonic element units) 4 that are provided on the substrate 2 so as to transmit and receive ultrasonic waves, and the acoustic matching section 6 that is provided on the substrate 2 on the side of the cell units 4 so as to cover each of the cell units 4.

Although the shape of the substrate 2 is not limited to a specific one, it forms a quadrangle in a planar view (in a planar view seen from the thickness direction of the substrate 2) in the configuration shown in the drawing. Also, as another shape of the substrate 2 in a planar view, another polygon such as a pentagon or a hexagon, a circle, or an ellipse can be listed, for example. Although the constituent material of the substrate 2 is not limited to a specific one, a material for forming a semiconductor such as silicon (Si) is used, for example. Consequently, it can be processed easily by etching or the like. Each cell unit 4 is arranged on the substrate 2 in a matrix pattern, that is, in a two-dimensionally pattern with predetermined intervals. In other words, a plurality of (three in the configuration shown in the drawing) cell units 4 are arranged in parallel along the X axis direction, and a plurality of (three in the configuration shown in the drawing) cell units 4 are arranged in parallel along the Y axis direction.

The cell unit 4 has a first ultrasonic element group 3a provided with "m" first ultrasonic elements (first ultrasonic vibrators) 8a, with "m" representing the number of the first ultrasonic elements and being an integer of 1 or more (one in the configuration shown in the drawing), that have first diaphragms 51a, and transmit and receive ultrasonic waves, a second ultrasonic element group 3b provided with "n" second ultrasonic elements (second ultrasonic vibrators) 8b, with "n" representing the number of the second ultrasonic elements and being an integer larger than "m" (four in the configuration shown in the drawing), that have second diaphragms 51b whose areas (areas in a planar view) are smaller than those of the first diaphragms 51a, and transmit and receive ultrasonic waves, and two third ultrasonic element groups 3c and 3d provided with "k" third ultrasonic elements (third ultrasonic vibrators) 8c, 8d, with "k" representing the number of the third ultrasonic elements and being an integer larger than "m" (nine in the configuration shown in the drawing), that have third diaphragms 51c and 51d whose areas (areas in a planar view) are smaller than those of the second diaphragms 51b, respectively, and transmit and receive ultrasonic waves. However, the number of the third ultrasonic element groups may be one.

Hereinafter, the first ultrasonic element group 3a, the second ultrasonic element group 3b, and the third ultrasonic element groups 3c and 3d are also referred to as "ultrasonic element group", respectively. Further, the first ultrasonic element 8a, the second ultrasonic element 8b, and the third ultrasonic elements 8c and 8d are also referred to as "ultrasonic element", respectively. Further, the first diaphragm 51a, the second diaphragm 51b, and the third diaphragms 51c and 51d are also referred to as "diaphragm", respectively.

The first ultrasonic element group 3a is disposed at the upper left, the second ultrasonic element group 3b is disposed at the lower right, the third ultrasonic element group 3c is disposed at the upper right, and the third ultrasonic element group 3d is disposed at the lower left, respectively. However, needless to say, the invention is not limited to this arrangement. Here, explanations will be made on the first ultrasonic element 8a, the second ultrasonic element 8b, and the third ultrasonic elements 8c and 8d. However, these ultrasonic elements 8a, 8b, 8c, and 8d have similar basic configurations although the sizes are different. Hereinafter, therefore, explanations will be made on the first ultrasonic element 8a as a representative. In FIG. 4 and FIG. 5, for the second ultrasonic element group 3b and the third ultrasonic element groups 3c and 3d, each section thereof that corresponds to each section of the first ultrasonic element group 3a is shown with a reference symbol "b", "c" or "d" instead of "a" at the end thereof with parenthesis.

As shown in FIG. 4 and FIG. 5, the first ultrasonic element 8a is constructed by the first diaphragm 51a and a piezoelectric body (piezoelectric element) 7a. The first ultrasonic element 8a is formed on the substrate 2. Although the shape of the piezoelectric body 7a is not limited to a specific one, it forms a circle in a planar view in the configuration shown in the drawing. Also, as another shape of the piezoelectric body 7a in a planar view, a quadrangle (square, rectangle), a polygon such as a pentagon or a hexagon, or an ellipse can be listed, for example. Incidentally, the piezoelectric body 7a and the wiring thereof will be described below. An opening 21 for forming the first diaphragm 51a of the first ultrasonic element 8a is formed in a part of the substrate 2 corresponding to each of the first ultrasonic element 8a. Although the shape of the opening 21 is not limited to a specific one, it forms a circle in a planar view in the configuration shown in the drawing. Also, as another shape of the opening 21 in a planar view, a quadrangle (square, rectangle), a polygon such as a pentagon or a hexagon, or an ellipse can be listed, for example.

A supporting film 5 is formed on the substrate 2, and each of the openings 21 is covered with the supporting film 5. The first diaphragm 51a is constructed by a part of the supporting film 5 corresponding to the opening which is a part (region) covering the opening 21, that is, a part coinciding with (part overlapping with) the opening 21 of the supporting film 5 in a planar view. The piezoelectric body 7a is provided on the first diaphragm 51a.

Although the constituent material of the supporting film 5 is not limited to a specific one, the supporting film 5 is constructed by a layered body (two-layer structure) of an $SiO_2$ layer and a $ZrO_2$ layer, or an $SiO_2$ layer, for example. In a case where the substrate 2 is an Si substrate, the $SiO_2$ layer can be formed by conducting a thermal oxidation treatment to the surface of the substrate 2. The $ZrO_2$ layer can be formed on the $SiO_2$ layer, for example, by a technique such as sputtering. Here, the $ZrO_2$ layer is a layer for preventing Pb that constitutes PZT from diffusing into the $SiO_2$ layer when PZT is used as a piezoelectric film 72a of the piezoelectric body 7a, for example. The piezoelectric film 72a of the piezoelectric body 7a will be described below. The $ZrO_2$ layer also has an effect such as an effect of improving deflection efficiency with respect to deformation of the piezoelectric film 72a.

As shown in FIG. 5, the piezoelectric body 7a has a lower electrode 71a formed on the first diaphragm 51a (the supporting film 5), the piezoelectric film 72a formed on the lower electrode 71a, and an upper electrode 73a formed on the piezoelectric film 72a. Also, a conducting wire (wiring) for a lower electrode 711a is connected with the lower electrode 71a, and the conducting wire for a lower electrode 711a extends along the Y axis direction on the supporting film 5 as shown in FIG. 4, for example. The conducting wire for a lower electrode 711a is electrically connected with the cable 210 via a through-hole formed in the supporting film 5 and the substrate 2. The through-hole is not shown in the drawing. With this configuration, the first ultrasonic element 8a (the first ultrasonic element group 3a) can be driven independently. Likewise, the second ultrasonic element group 3b and the third ultrasonic element groups 3c and 3d can be driven independently.

In the second ultrasonic element group 3b, each second ultrasonic element 8b is electrically connected in series by a conducting wire for a lower electrode 711b. In this case, the conducting wire for a lower electrode 711b is interposed between lower electrodes 71b of two adjacent second ultrasonic elements 8b, and the lower electrodes 71b of the two adjacent second ultrasonic elements 8b are electrically connected by the conducting wire for a lower electrode 711b.

Likewise, in the third ultrasonic element group 3c, each third ultrasonic element 8c is electrically connected in series by a conducting wire for a lower electrode 711c. In this case, the conducting wire for a lower electrode 711c is interposed between lower electrodes 71c of two adjacent third ultrasonic elements 8c, and the lower electrodes 71c of the two adjacent third ultrasonic elements 8c are electrically connected by the conducting wire for a lower electrode 711c.

Likewise, in the third ultrasonic element group 3d, each third ultrasonic element 8d is electrically connected in series by a conducting wire for a lower electrode 711d. In this case, the conducting wire for a lower electrode 711d is interposed between lower electrodes 71d of two adjacent third ultrasonic elements 8d, and the lower electrodes 71d of the two adjacent third ultrasonic elements 8d are electrically connected by the conducting wire for a lower electrode 711d.

As shown in FIG. 4 and FIG. 5, for example, a conducting wire (wiring) for an upper electrode 731a is connected with the upper electrodes 73a, 73b, 73c and 73d, and the conducting wire for an upper electrode 731a extends along the X axis direction on the supporting film 5. The conducting wire for an upper electrode 731a serves as a common conducting wire of each first ultrasonic element 8a (the first ultrasonic element group 3a), the second ultrasonic element group 3b, the third ultrasonic element group 3c, and the third ultrasonic element group 3d arranged in the X axis direction, and is connected to the GND, for example, at the end portion thereof. In this manner, the upper electrodes 73a, 73b, 73c and 73d of the ultrasonic element 8a, 8b, 8c and 8d are earthed. Alternatively, contrary to the above, the conducting wires for a lower electrode 711a, 711b, 711c, and 711d may be connected to the GND.

The constituent materials of the lower electrode 71a, the upper electrode 73a, the conducting wire for a lower electrode 711a, and the conducting wire for an upper electrode 731a are not limited to specific ones as long as they have conductive properties, respectively. For example, various kinds of metal materials can be used. Also, the lower electrode 71a, the upper electrode 73a, the conducting wire for a lower electrode 711a, and the conducting wire for an upper electrode 731a may be single layers, respectively, or may be layered bodies in which a plurality of layers are laminated, respectively. As specific examples, for example, a Ti/Ir/Pt/Ti layered film can be used as the lower electrode 71a and the conducting wire for a lower electrode 711a, respectively, and an Ir film can be used as the upper electrode 73a and the conducting wire for an upper electrode 731a, respectively.

The piezoelectric film 72a is made by forming PZT (lead zirconate titanate) into a film shape, for example. In the present embodiment, PZT is used as the piezoelectric film 72a. However, any material can be used as long as it is a material that can contract (expand or contract) in an in-plane direction by applying a voltage thereto. For example, lead titanate (PbTiO$_3$), lead zirconate (PbZrO$_3$), lead lanthanum titanate ((Pb, La) TiO$_3$), or the like can be used as well as PZT.

In the first ultrasonic element 8a, for example, when a voltage is applied between the lower electrode 71a and the upper electrode 73a by the device main body 300 (see FIG. 6, FIG. 7) through the cable 210, the piezoelectric film 72a expands or contracts in the in-plane direction. In this instance, a surface of the piezoelectric film 72a is attached to the supporting film 5 through the lower electrode 71a, and the upper electrode 73a is formed on the other surface thereof. Here, since any other layer is not formed on the upper electrode 73a, the supporting film 5 side of the piezoelectric film 72a does not easily expand or contract, while the upper electrode 73a side of the piezoelectric film 72a easily expands or contracts. Therefore, when a voltage is applied to the piezoelectric film 72a, deflection that causes projection occurs on the opening 21 side, which results in deflection of the first diaphragm 51a. Consequently, when an alternating voltage is applied to the piezoelectric film 72a, the first diaphragm 51a vibrates with respect to the film thickness direction, and this vibration of the first diaphragm 51a transmits (sends) ultrasonic waves.

In transmission of such ultrasonic waves, an alternating voltage, whose frequency is equal to the resonance frequency of the first ultrasonic element 8a, or is close to the resonance frequency and is smaller than the resonance frequency, is applied to the piezoelectric film 72a, and the first ultrasonic element 8a is resonantly driven. With this, the first diaphragm 51a is greatly deflected, so that ultrasonic waves can be transmitted with high output. Preferably, in this case, the frequency of the alternating voltage applied to the first ultrasonic element 8a is between 0.5 times and 0.9 times with respect to the resonance frequency of the first ultrasonic element 8a. If the frequency of the alternating voltage is less than 0.5 times with respect to the resonance frequency of the first ultrasonic element 8a, the output of the transmitted ultrasonic waves will become small and the waveform of the ultrasonic waves will easily be disturbed depending on other conditions. On the other hand, if the frequency of the alternating voltage is more than 0.9 times with respect to the resonance frequency of the first ultrasonic element 8a, the first ultrasonic element 8a will easily be damaged depending on other conditions.

In receiving ultrasonic waves with the first ultrasonic element 8a, when ultrasonic waves are input to the first diaphragm 51a, the first diaphragm 51a vibrates with respect to the film thickness direction. In the first ultrasonic element 8a, this vibration of the first diaphragm 51a causes a potential difference between the surface of the piezoelectric film 72a on the lower electrode 71a side and the surface of the piezoelectric film 72a on the upper electrode 73a, and a reception signal (detection signal) (current) is output from the upper electrode 73a and the lower electrode 71a in response to the displacement amount of the piezoelectric film 72a. This signal is transmitted to the device main body 300 (see FIG. 6, FIG. 7) through the cable 210, and predetermined signal processing or the like is conducted based on the signal. Then, in the device main body 300, an ultrasonic image (electronic image) is formed and displayed.

In the ultrasonic probe 10, planar waves of ultrasonic waves can be transmitted in a desired direction by delaying and differentiating the timing of transmission of ultrasonic waves from each cell unit 4 arranged in parallel along the X axis direction. Here, when the area of the first diaphragm 51a of the first ultrasonic element 8a is "S1", the area of the second diaphragm 51b of the second ultrasonic element 8b is "S2", and the area of the third diaphragms 51c, 51d of the third ultrasonic elements 8c, 8d is "S3", it is sufficient for them to satisfy S1>S2>S3. Preferably, however, S2/S1 is within the range of 0.2 to 0.8, and more preferably, S2/S1 is within the range of 0.3 to 0.6. Also, preferably, S3/S1 is within the range of 0.1 to 0.5, and more preferably, S3/S1 is within the range of 0.2 to 0.4.

Also, when the resonance frequency of the first ultrasonic element 8a is "F1", the resonance frequency of the second ultrasonic element 8b is "F2", and the resonance frequency of the third ultrasonic elements 8c, 8d is "F3" (F1<F2<F3), it is preferable to set S1, S2, and S3, respectively, such that F3 becomes the least common multiple of F1 and F2. The number of the second ultrasonic element 8b of the second ultrasonic element group 3b is greater than the number of the first ultrasonic element 8a of the first ultrasonic element group 3a. In the present embodiment, the second ultrasonic element group 3b has three or more second ultrasonic elements 8b, and more specifically, the second ultrasonic element group 3b has four second ultrasonic elements 8b.

The numbers of the third ultrasonic elements 8c, 8d of the third ultrasonic element groups 3c, 3d are greater than the number of the second ultrasonic element 8b of the second ultrasonic element group 3b, respectively. In the present embodiment, the third ultrasonic element groups 3c, 3d have four or more third ultrasonic elements 8c, 8d, and more specifically, the third ultrasonic element groups 3c, 3d have nine third ultrasonic elements 8c, 8d, respectively. Here, the number of the second ultrasonic element 8b of the second ultrasonic element group 3b is not limited to a specific one as long as it is greater than the number of the first ultrasonic element 8a of the first ultrasonic element group 3a. Preferably, however, the number of the second ultrasonic element 8b of the second ultrasonic element group 3b is between 4 and 6.

The numbers of the third ultrasonic elements 8c, 8d of the third ultrasonic element groups 3c, 3d are not limited to specific ones as long as they are greater than the number of the second ultrasonic element 8b of the second ultrasonic element group 3b, respectively. Preferably, however, the numbers of the third ultrasonic elements 8c, 8d of the third ultrasonic element groups 3c, 3d are between 5 to 10. When the total sum of the areas of the first diaphragms 51a of the first ultrasonic element group 3a is "A" and the total sum of the areas of the second diaphragms 51b of the second ultrasonic element group 3b is "B", B/A is within the range of 0.9 to 1.1. With this configuration, since the sensitivity of the first ultrasonic element 8a depends on the area of the first diaphragm 51a, the sensitivity of the first ultrasonic element group 3a and the sensitivity of the second ultrasonic element group 3b can be made substantially the same. Consequently, a circuit needed for matching the magnitude of a signal in a case where the sensitivity is different can be omitted, and thus the circuit configuration can be simplified.

Preferably, B/A is within the range of 0.95 to 1.05. In this case, since the difference between the noise level of the first ultrasonic element group 3a and the noise level of the second ultrasonic element group 3b is small, there is no need to conduct fine adjustment so as to compare each signal when displaying a tomographic image. Therefore, the circuit configuration can further be simplified. When the total sum of the areas of the third diaphragms 51c, 51d of the third ultrasonic element groups 3c, 3d is "C", C/A is within the range of 0.9 to 1.1. With this configuration, the sensitivity of the first ultrasonic element group 3a and the sensitivity of the third ultrasonic element groups 3c, 3d can be made substantially the same. Consequently, a circuit needed for matching the magnitude of a signal in a case where the sensitivity is different can be omitted, and thus the circuit configuration can be simplified.

Preferably, C/A is within the range of 0.95 to 1.05. In this case, since the difference between the noise level of the first ultrasonic element group 3a and the noise level of the third ultrasonic element group 3c is small, there is no need to conduct fine adjustment so as to compare each signal when displaying a tomographic image. Therefore, the circuit configuration can further be simplified. Also, preferably, the conducting wire for a lower electrode 711b that is a wiring for electrically connecting each second ultrasonic element 8b of the second ultrasonic element group 3b in series is provided such that the total sum of distances Lb of the conducting wires for a lower electrode 711b between two adjacent second ultrasonic elements 8b which are electrically connected with each other becomes shortest. With this configuration, the voltage drop in the conducting wire for a lower electrode 711b can be reduced.

In the present embodiment, each second ultrasonic element 8b of the second ultrasonic element group 3b is connected by the conducting wire for a lower electrode 711b as shown in FIG. 3. This configuration meets the conditions that the total sum of the distances Lb is shortest. Likewise, preferably, the conducting wire for a lower electrode 711c that is a wiring for electrically connecting each third ultrasonic element 8c of the third ultrasonic element group 3c in series is provided such that the total sum of distances Lc of the conducting wires for a lower electrode 711c between two adjacent third ultrasonic elements 8c which are electrically connected with each other becomes shortest. With this configuration, the voltage drop in the conducting wire for a lower electrode 711c can be reduced.

In the present embodiment, each third ultrasonic element 8c of the third ultrasonic element group 3c is connected by the conducting wire for a lower electrode 711c in a zigzag pattern as shown in FIG. 3. This configuration meets the conditions that the total sum of the distances Lc is shortest. Likewise, preferably, the conducting wire for a lower electrode 711d that is a wiring for electrically connecting each third ultrasonic element 8d of the third ultrasonic element group 3d in series is provided such that the total sum of distances Ld of the conducting wires for a lower electrode 711d between two adjacent third ultrasonic elements 8d which are electrically connected with each other becomes shortest. With this configuration, the voltage drop in the conducting wire for a lower electrode 711d can be reduced.

In the present embodiment, each third ultrasonic element 8d of the third ultrasonic element group 3d is connected by the conducting wire for a lower electrode 711d in a zigzag pattern as shown in FIG. 3. This configuration meets the conditions that the total sum of the distances Ld is shortest. Here, as the pattern of the conducting wire for a lower electrode 711c, 711d that makes the total sum of the distances Lc or Ld shortest, a spiral pattern can be listed, for example, as well as the above pattern.

Preferably, in the conducting wire for a lower electrode 711b that is a wiring for electrically connecting each second ultrasonic element 8b of the second ultrasonic element group 3b in series, all of the distances Lb of the conducting wires for a lower electrode 711b between two adjacent second ultrasonic elements 8b of the second ultrasonic element group 3b which are electrically connected with each other are the same. With this configuration, the phase difference of ultrasonic waves between two adjacent second ultrasonic elements 8b which are electrically connected with each other can be made the same in the second ultrasonic element group 3b, and thus designing can be conducted easily.

Likewise, preferably, in the conducting wire for a lower electrode 711c that is a wiring for electrically connecting each third ultrasonic element 8c of the third ultrasonic element group 3c in series, all of the distances Lc of the conducting wires for a lower electrode 711c between two adjacent third ultrasonic elements 8c of the third ultrasonic element group 3c which are electrically connected with each other are the same. With this configuration, the phase difference of ultrasonic waves between two adjacent third ultrasonic elements 8c which are electrically connected with each other can be made the same in the third ultrasonic element group 3c, and thus designing can be conducted easily.

Likewise, preferably, in the conducting wire for a lower electrode 711d that is a wiring for electrically connecting each third ultrasonic element 8d of the third ultrasonic element group 3d in series, all of the distances Ld of the conducting wires for a lower electrode 711d between two adjacent third ultrasonic elements 8d of the third ultrasonic element group 3d which are electrically connected with each other are the same. With this configuration, the phase difference of ultrasonic waves between two adjacent third ultrasonic elements 8d which are electrically connected with each other can be made the same in the third ultrasonic element group 3d, and thus designing can be conducted easily.

Also, preferably, the distance Lc and the distance Ld are the same. With this configuration, the phase difference of ultrasonic waves between two adjacent third ultrasonic elements 8c of the third ultrasonic element group 3c which are electrically connected with each other and the phase difference of ultrasonic waves between two adjacent third ultrasonic elements 8d of the third ultrasonic element group 3d which are electrically connected with each other can be made the same. Therefore, designing can be conducted easily.

Also, preferably, the distance Lb, the distance Lc, and the distance Ld are the same. With this configuration, the phase difference of ultrasonic waves between two adjacent second ultrasonic elements 8b of the second ultrasonic element group 3b which are electrically connected with each other, the phase difference of ultrasonic waves between two adjacent third ultrasonic elements 8c of the third ultrasonic element group 3c which are electrically connected with each other, and the phase difference of ultrasonic waves between two adjacent third ultrasonic elements 8d of the third ultrasonic element group 3d which are electrically connected with each other can be made the same. Therefore, designing can be conducted easily. Here, the above-described expression that "distances are the same" includes a case where the distances are almost the same and a case where the distances are substantially the same as well as a case where the distances are completely the same.

Next, explanations will be made on a usage example of a case where the ultrasonic probe 10 is applied to the diagnostic device 100 described below. In this case, the third ultrasonic element group 3d is not used. In transmission of ultrasonic waves, any one of the first ultrasonic element group 3a, the second ultrasonic element group 3b, and the third ultrasonic element group 3c is selected and used. In reception of ultrasonic waves, any one of the first ultrasonic element group 3a, the second ultrasonic element group 3b, and the third ultrasonic element group 3c is selected and used. As a display mode, either one of a B (brightness) mode and a harmonic mode is used. Such a case will be explained.

However, the third ultrasonic element group 3d may be used instead of the third ultrasonic element group 3c. Further, both of the third ultrasonic element group 3c and the third ultrasonic element group 3d may be used. The B mode is a display mode which displays an image by changing the intensity of the received ultrasonic waves into brightness (by conducting brightness modulation).

When ultrasonic waves propagate through a living body, the waveform is deformed due to the difference in speed of the ultrasonic waves propagating the living body, which causes high harmonic components with respect to the transmitted ultrasonic waves. The harmonic mode is a display mode which displays an image by receiving the high harmonic components with respect to the transmitted ultrasonic waves. Normally, in the harmonic mode, second harmonic waves, having frequency of twice as much as fundamental waves which are ultrasonic waves to be transmitted or third harmonic waves having frequency of three times, are received. In a case of diagnosing a part of a long distance, the harmonic mode is not used because high harmonic waves are hardly generated. In the harmonic mode, since high harmonic waves are received, the sensitivity can be improved and good ultrasonic images can be obtained.

The resonance frequency of the first ultrasonic element group 3a is 1.00 MHz, the resonance frequency of the second ultrasonic element group 3b is 1.50 MHz, and the resonance frequencies of the third ultrasonic element groups 3c and 3d are 3.00 MHz, respectively. Incidentally, 0.5 times-0.9 times of the resonance frequency of the first ultrasonic element group 3a is 0.50 MHz-0.90 MHz. 0.5 times-0.9 times of the resonance frequency of the second ultrasonic element group 3b is 0.75 MHz-1.35 MHz. 0.5 times-0.9 times of the resonance frequencies of the third ultrasonic element groups 3c and 3d are 1.5 MHz-2.70 MHz, respectively.

In the following explanations, a long distance refers to a distance that is more than 200 mm and equal to or less than 300 mm. A middle distance refers to a distance that is more than 50 mm and equal to or less than 200 mm. A short distance refers to a distance that is equal to or less than 50 mm. In the ultrasonic probe 10, ultrasonic waves can be transmitted and received at various frequencies by changing the combination of the ultrasonic element group that transmits ultrasonic waves and the ultrasonic element group that receives ultrasonic waves, and thus various ultrasonic images can be obtained by using ultrasonic waves of various frequencies. Therefore, the same ultrasonic probe 10 can be used for diagnosis of parts of a short distance, a middle distance, and a long distance, respectively, without replacing the ultrasonic probe 10. Accordingly, a laborious process to an operator can be reduced.

When a part of a short distance is diagnosed, ultrasonic waves are transmitted by the third ultrasonic element group 3c that can generate ultrasonic waves of high frequency, and ultrasonic waves are received by the same third ultrasonic element group 3c, for example. Consequently, the resolution can be improved, and a good image of a part of a short distance can be obtained. Further, when a part of a long distance is diagnosed, ultrasonic waves are transmitted by the first ultrasonic element group 3a or the second ultrasonic element group 3b, and ultrasonic waves are received by the first ultrasonic element group 3a, the second ultrasonic element group 3b, or the third ultrasonic element group 3c, for example. Consequently, a good image of a part of a long distance can be obtained. Further, when the harmonic mode is used, and ultrasonic waves are received by the second ultrasonic element group 3b or the third ultrasonic element group 3c, for example, a good image of a part of a middle distance or a long distance can be obtained. Next, specific examples will be explained based on Table 1 shown below.

TABLE 1

| | Transmitting ultrasonic element group | Receiving ultrasonic element group | Mode | Range | Transmission frequency (MHz) | Reception frequency (MHz) |
|---|---|---|---|---|---|---|
| Configuration 1 | 3a | 3a | B mode | Long distance | 0.60 | 0.60 |
| Configuration 2 | 3a | 3a | B mode | Long distance | 0.75 | 0.75 |
| Configuration 3 | 3a | 3a | B mode | Middle distance | 0.90 | 0.90 |
| Configuration 4 | 3a | 3b | Harmonic | Long distance | 0.60 | 1.20 |
| Configuration 5 | 3a | 3b | Harmonic | Middle distance | 0.75 | 1.50 |
| Configuration 6 | 3a | 3c | Harmonic | Long distance | 0.60 | 1.80 |
| Configuration 7 | 3b | 3b | B mode | Middle distance | 0.90 | 0.90 |
| Configuration 8 | 3b | 3a | B mode | Middle distance | 0.90 | 0.90 |
| Configuration 9 | 3b | 3b | B mode | Middle distance | 1.20 | 1.20 |
| Configuration 10 | 3b | 3b | B mode | Middle distance | 1.35 | 1.35 |
| Configuration 11 | 3b | 3c | Harmonic | Long distance | 1.20 | 2.40 |
| Configuration 12 | 3b | 3c | Harmonic | Long distance | 1.35 | 2.70 |
| Configuration 13 | 3b | 3c | Harmonic | Long distance | 1.00 | 3.00 |
| Configuration 14 | 3c | 3c | B mode | Short distance | 1.80 | 1.80 |
| Configuration 15 | 3c | 3c | B mode | Short distance | 2.40 | 2.40 |
| Configuration 16 | 3c | 3c | B mode | Short distance | 2.70 | 2.70 |

As shown in Table 1, in Configuration 1, the B mode is used, ultrasonic waves are transmitted by the first ultrasonic element group 3a, and ultrasonic waves are received by the first ultrasonic element group 3a. This configuration is used for diagnosis of a part of a long distance. The frequency of the transmitted ultrasonic waves is 0.60 MHz, for example, and the frequency of the received ultrasonic waves is 0.60 MHz, for example. In Configuration 2, the B mode is used, ultrasonic waves are transmitted by the first ultrasonic element group 3a, and ultrasonic waves are received by the first ultrasonic element group 3a. This configuration is used for diagnosis of a part of a long distance. The frequency of the transmitted ultrasonic waves is 0.75 MHz, for example, and the frequency of the received ultrasonic waves is 0.75 MHz, for example.

In Configuration 3, the B mode is used, ultrasonic waves are transmitted by the first ultrasonic element group 3a, and ultrasonic waves are received by the first ultrasonic element group 3a. This configuration is used for diagnosis of a part of a middle distance. The frequency of the transmitted ultrasonic waves is 0.90 MHz, for example, and the frequency of the received ultrasonic waves is 0.90 MHz, for example. In Configuration 4, the harmonic mode is used, ultrasonic waves are transmitted by the first ultrasonic element group 3a, and ultrasonic waves are received by the second ultrasonic element group 3b. This configuration is used for diagnosis of a part of a long distance. The frequency of the transmitted ultrasonic waves is 0.60 MHz, for example, and the frequency of the received ultrasonic waves is 1.20 MHz, for example.

In Configuration 5, the harmonic mode is used, ultrasonic waves are transmitted by the first ultrasonic element group 3a, and ultrasonic waves are received by the second ultrasonic element group 3b. This configuration is used for diagnosis of a part of a middle distance. The frequency of the transmitted ultrasonic waves is 0.75 MHz, for example, and the frequency of the received ultrasonic waves is 1.50 MHz, for example. In Configuration 6, the harmonic mode is used, ultrasonic waves are transmitted by the first ultrasonic element group 3a, and ultrasonic waves are received by the third ultrasonic element group 3c. This configuration is used for diagnosis of a part of a long distance. The frequency of the transmitted ultrasonic waves is 0.60 MHz, for example, and the frequency of the received ultrasonic waves is 1.80 MHz, for example.

In Configuration 7, the B mode is used, ultrasonic waves are transmitted by the second ultrasonic element group 3b, and ultrasonic waves are received by the second ultrasonic element group 3b. This configuration is used for diagnosis of a part of a middle distance. The frequency of the transmitted ultrasonic waves is 0.90 MHz, for example, and the frequency of the received ultrasonic waves is 0.90 MHz, for example. In Configuration 8, the B mode is used, ultrasonic waves are transmitted by the second ultrasonic element group 3b, and ultrasonic waves are received by the first ultrasonic element group 3a. This configuration is used for diagnosis of a part of a middle distance. The frequency of the transmitted ultrasonic waves is 0.90 MHz, for example, and the frequency of the received ultrasonic waves is 0.90 MHz, for example.

In Configuration 9, the B mode is used, ultrasonic waves are transmitted by the second ultrasonic element group 3b, and ultrasonic waves are received by the second ultrasonic element group 3b. This configuration is used for diagnosis of a part of a middle distance. The frequency of the transmitted ultrasonic waves is 1.20 MHz, for example, and the frequency of the received ultrasonic waves is 1.20 MHz, for example. In Configuration 10, the B mode is used, ultrasonic waves are transmitted by the second ultrasonic element group 3b, and ultrasonic waves are received by the second ultrasonic element group 3b. This configuration is used for diagnosis of a part of a middle distance. The frequency of the transmitted ultrasonic waves is 1.35 MHz, for example, and the frequency of the received ultrasonic waves is 1.35 MHz, for example.

In Configuration 11, the harmonic mode is used, ultrasonic waves are transmitted by the second ultrasonic element group 3b, and ultrasonic waves are received by the third ultrasonic element group 3c. This configuration is used for diagnosis of a part of a long distance. The frequency of the transmitted ultrasonic waves is 1.20 MHz, for example, and the frequency of the received ultrasonic waves is 2.40 MHz, for example. In Configuration 12, the harmonic mode is used, ultrasonic waves are transmitted by the second ultrasonic element group 3b, and ultrasonic waves are received by the third ultrasonic element group 3c. This configuration is used for diagnosis of a part of a long distance. The frequency of the transmitted ultrasonic waves is 1.35 MHz, for example, and the frequency of the received ultrasonic waves is 2.70 MHz, for example.

In Configuration 13, the harmonic mode is used, ultrasonic waves are transmitted by the second ultrasonic element group 3b, and ultrasonic waves are received by the third ultrasonic element group 3c. This configuration is used for diagnosis of a part of a long distance. The frequency of the transmitted ultrasonic waves is 1.00 MHz, for example, and the frequency of the received ultrasonic waves is 3.00 MHz, for example. In Configuration 14, the B mode is used, ultrasonic waves are transmitted by the third ultrasonic element group 3c, and ultrasonic waves are received by the third ultrasonic element group 3c. This configuration is used for diagnosis of a part of a short distance. The frequency of the transmitted ultrasonic waves is 1.80 MHz, for example, and the frequency of the received ultrasonic waves is 1.80 MHz, for example.

In Configuration 15, the B mode is used, ultrasonic waves are transmitted by the third ultrasonic element group 3c, and ultrasonic waves are received by the third ultrasonic element group 3c. This configuration is used for diagnosis of a part of a short distance. The frequency of the transmitted ultrasonic waves is 2.40 MHz, for example, and the frequency of the received ultrasonic waves is 2.40 MHz, for example. In Configuration 16, the B mode is used, ultrasonic waves are transmitted by the third ultrasonic element group 3c, and ultrasonic waves are received by the third ultrasonic element group 3c. This configuration is used for diagnosis of a part of a short distance. The frequency of the transmitted ultrasonic waves is 2.70 MHz, for example, and the frequency of the received ultrasonic waves is 2.70 MHz, for example.

In the above examples, any one of the first ultrasonic element group 3a, the second ultrasonic element group 3b, and the third ultrasonic element group 3c is selected and used for transmission of ultrasonic waves, and any one of the first ultrasonic element group 3a, the second ultrasonic element group 3b, and the third ultrasonic element group 3c is selected and used for reception of ultrasonic waves. However, the invention is not limited to these examples. Any two of the first ultrasonic element group 3a, the second ultrasonic element group 3b, and the third ultrasonic element group 3c may be selected and used, or all of them may be used, for transmission of ultrasonic waves. Also, any two of the first ultrasonic element group 3a, the second ultrasonic element group 3b, and the third ultrasonic element group 3c may be selected and used, or all of them may be used, for reception of ultrasonic waves.

Modification Example of Ultrasonic Transducer

In the ultrasonic transducer 1 according to the above-described embodiment, the number of the first ultrasonic element 8a of the first ultrasonic element group 3a is one. However, the number may be two, or may be three or more. Here, explanations will be made on a case where the number of the first ultrasonic element 8a of the first ultrasonic element group 3a is three or more in the ultrasonic transducer 1.

Preferably, the conducting wire for a lower electrode 711a that is a wiring for electrically connecting each first ultrasonic element 8a of the first ultrasonic element group 3a in series is provided such that the total sum of distances of the conducting wires for a lower electrode 711a between two adjacent first ultrasonic elements 8a which are electrically connected with each other becomes shortest. With this configuration, the voltage drop in the conducting wire for a lower electrode 711a can be reduced.

Preferably, in the conducting wire for a lower electrode 711a that is a wiring for electrically connecting each first ultrasonic element 8a of the first ultrasonic element group 3a in series, all of the distances of the conducting wires for a lower electrode 711a between two adjacent first ultrasonic elements 8a of the first ultrasonic element group 3a which are electrically connected with each other are the same. With this configuration, the phase difference of ultrasonic waves between two adjacent first ultrasonic elements 8a which are electrically connected with each other can be made the same in the first ultrasonic element group 3a, and thus designing can be conducted easily.

Also, preferably, the distance of the conducting wire for a lower electrode 711a between two adjacent first ultrasonic elements 8a of the first ultrasonic element group 3a which are electrically connected with each other, the distance Lb, the distance Lc, and the distance Ld are the same. With this configuration, the phase difference of ultrasonic waves between two adjacent first ultrasonic elements 8a of the first ultrasonic element group 3a which are electrically connected with each other, the phase difference of ultrasonic waves between two adjacent second ultrasonic elements 8b of the second ultrasonic element group 3b which are electrically connected with each other, the phase difference of ultrasonic waves between two adjacent third ultrasonic elements 8c of the third ultrasonic element group 3c which are electrically connected with each other, and the phase difference of ultrasonic waves between two adjacent third ultrasonic elements 8d of the third ultrasonic element group 3d which are electrically connected with each other can be made the same. Therefore, designing can be conducted easily. The ultrasonic probe 10 and the ultrasonic transducer 1 described above can be applied to various kinds of electronic instruments such as diagnostic devices in a preferred manner. Hereinafter, an embodiment of a diagnostic device will be explained as a representative of an embodiment of an electronic instrument.

Embodiment of Diagnostic Device (Electronic Instrument)

Figure 6:
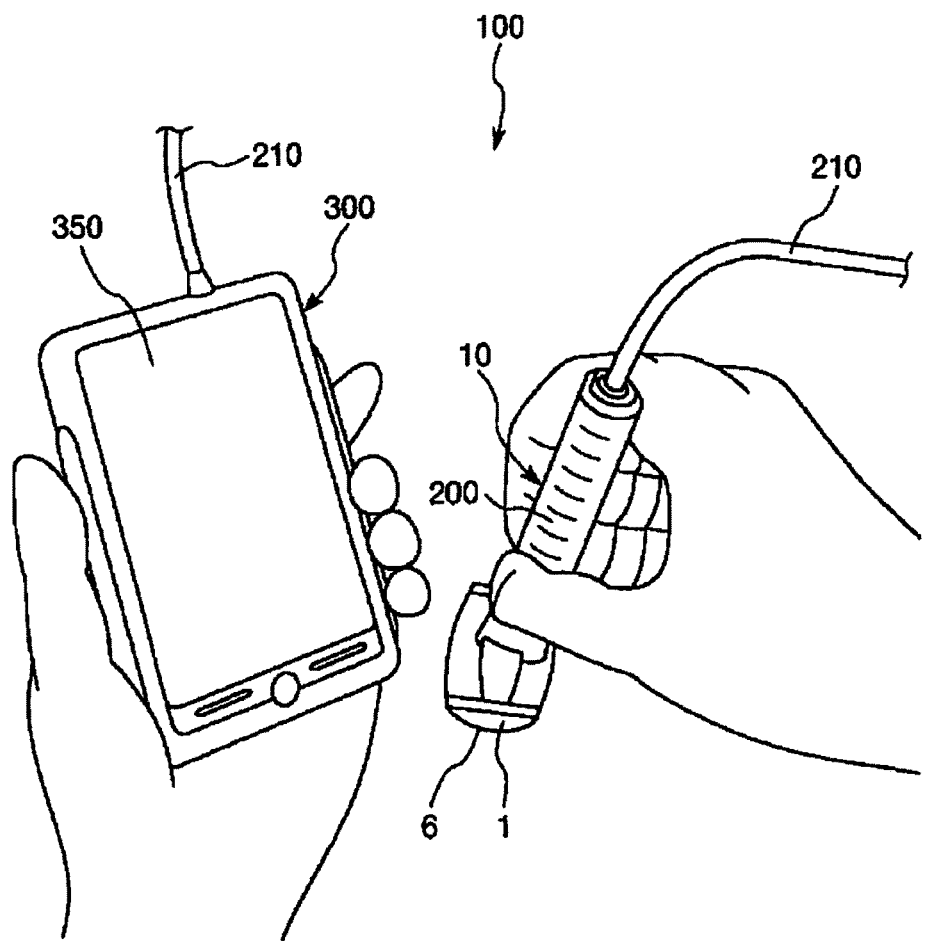
FIG. 6 is a perspective view showing an embodiment of a diagnostic device according to the invention.
Figure 7:
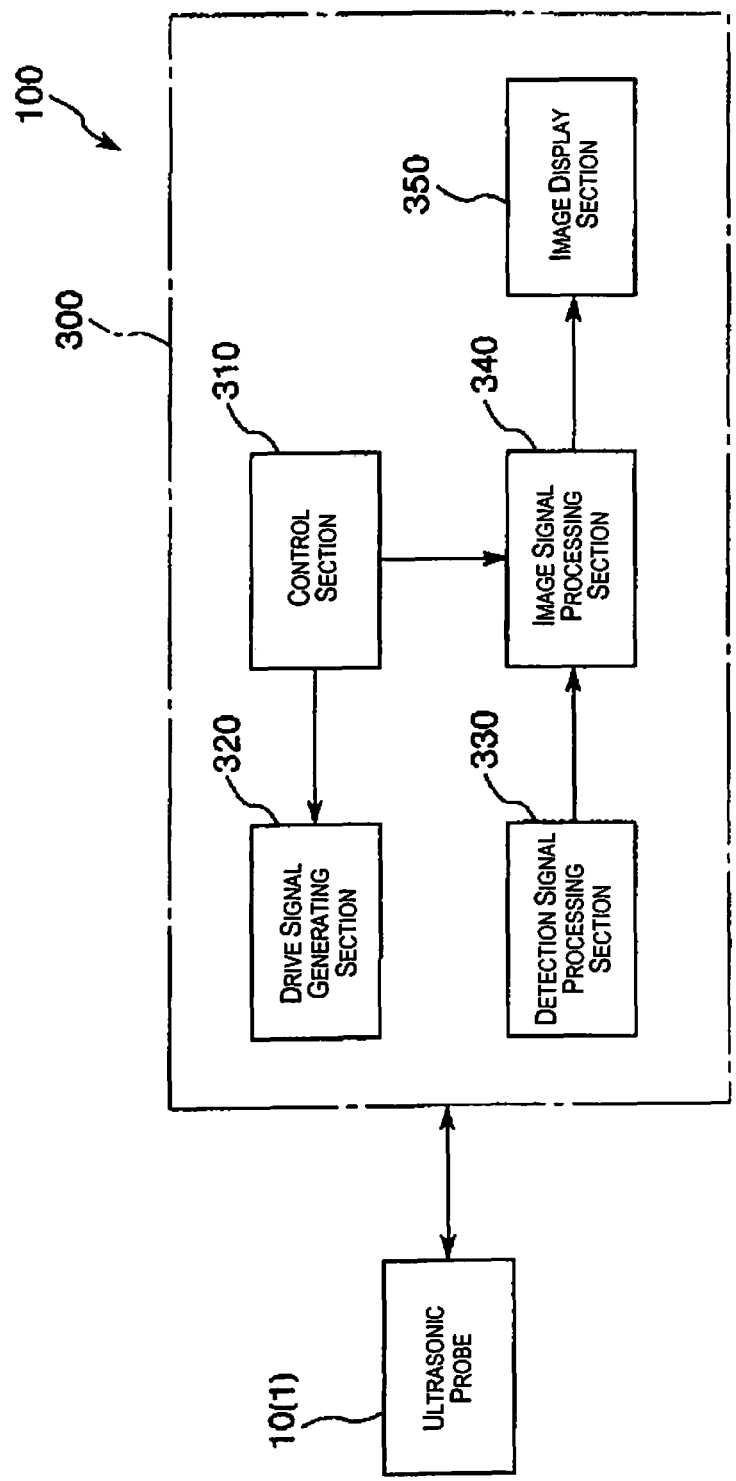
FIG. 7 is a block diagram showing the embodiment of the diagnostic device according to the invention.

FIG. 6 is a perspective view showing an embodiment of the diagnostic device according to the invention. FIG. 7 is a block diagram showing the embodiment of the diagnostic device according to the invention. As shown in FIG. 6 and FIG. 7, the diagnostic device 100 has the above-described ultrasonic probe 10, and the device main body 300 which is electrically connected with the ultrasonic probe 10 through the cable 210.

The device main body 300 has a control section (control means) 310, a drive signal generating section 320, a detection signal processing section 330, an image signal processing section 340, and an image display section (display means) 350. The signal processing section is constructed of the detection signal processing section 330 and the image signal processing section 340. The control section 310 is constructed of a microcomputer and the like, for example, and controls the entire device main body 300 such as the drive signal generating section 320 and the image signal processing section 340. The image display section 350 is constructed of a display device such as a CRT or an LCD, for example.

Next, the operation of the diagnostic device 100 will be explained. In conducting a test, the surface of the acoustic matching section 6 of the ultrasonic probe 10 is applied to a living body as a test target, and the diagnostic device 100 is activated. First, the control section 310 outputs a transmission order to the drive signal generating section 320, the drive signal generating section 320 transmits a drive signal for driving each ultrasonic element 8 to the ultrasonic element 8 at a predetermined timing. In this manner, each of the ultrasonic elements 8 is driven at a predetermined timing. Then, ultrasonic waves are transmitted from the ultrasonic transducer 1 of the ultrasonic probe 10.

The transmitted ultrasonic waves propagate through a living body, and the ultrasonic waves reflected on a predetermined part of the living body are input to the ultrasonic transducer 1 of the ultrasonic probe 10. Then, a detection signal corresponding to the input ultrasonic waves are output from the ultrasonic transducer 1. The detection signal is transmitted to the detection signal processing section 330 of the device main body 300 through the cable 210. The detection signal undergoes predetermined signal processing in the detection signal processing section 330, and is converted into a digital signal by an A/D converter included in the detection signal processing section 330. The A/D converter is not shown in the drawing.

The digital signal output from the detection signal processing section 330 is input to the image signal processing section 340, and is sequentially stored in a primary storing section included in the image signal processing section 340 as areal data in synchronization with a frame timing signal. The primary storing section is not shown in the drawing. The image signal processing section 340 reconstructs two-dimensional or three-dimensional image data based on each areal data, and also conducts image processing such as interpolation, response emphasis processing, or tone processing to the image data. The image data, to which image processing has been conducted, is stored in a secondary storing section included in the image signal processing section 340. The secondary storing section is not shown in the drawing.

The image data, to which image processing has been conducted, is then read out from the secondary storing section of the image signal processing section 340 and is input to the image display section 350. The image display section 350 displays an image based on the image data. A medical service worker such as a doctor conducts diagnosis or the like by observing an image displayed on the image display section 350. The invention is not limited to the ultrasonic transducer, the ultrasonic probe, the diagnostic device, and the electronic instrument of the invention explained in the above based on the embodiment shown in the drawing. The configuration of each section can be replaced with any configuration that has a similar function. Also, another optional element may be added to the invention.

In the above-described embodiment, the cell unit is arranged two-dimensionally. However, the invention is not limited to this, and the cell unit can be arranged one-dimensionally, for example. Further, in the above-described embodiment, the cell units are plural. However, the invention is not limited to this, and the cell unit may be single. Further, in the above-described embodiment, the cell unit has three kinds (three sizes) of ultrasonic element groups in which the areas of the diaphragms are different. However, the invention is not limited to this, and the cell unit may have two kinds (two sizes) of ultrasonic element groups in which the areas of the diaphragms are different, or may have four or more kinds (four or more sizes) of ultrasonic element groups in which the areas of the diaphragms are different.

In the above-described embodiment, the ultrasonic element of the first ultrasonic element group is single. However, the invention is not limited to this, and a plurality of ultrasonic elements may be provided in the first ultrasonic element group. In such a case, the first ultrasonic elements of the first ultrasonic element group are electrically connected in series. Further, according to the invention, the ultrasonic transducer (the ultrasonic probe) is not limited to a contact type sensor that is used by being brought into contact with a test target, and can be applied to a non-contact type sensor such as a proximity sensor that is used without being brought into contact with a test target.

According to one aspect of the embodiment, an ultrasonic transducer of the embodiment includes "m" first ultrasonic elements and "n" second ultrasonic elements. The "m" first ultrasonic elements includes first diaphragms. The "m" first ultrasonic elements are configured and arranged to transmit and receive ultrasonic waves, where "m" represents a number of the first ultrasonic elements and is an integer of 1 or more. Each of the first diaphragms having a first area. The "n" second ultrasonic elements include second diaphragms. Each of the "n" second diaphragms has a second area being smaller than the first area. The "n" second ultrasonic elements are configured and arranged to transmit and receive the ultrasonic waves, where "n" represents a number of the second ultrasonic elements and is an integer larger than "m". The "m" first ultrasonic elements are electrically connected in series in a case where "m" is an integer of 2 or more. The "n" second ultrasonic elements are electrically connected in series. B/A is within a range of 0.9 to 1.1, when a total sum of the first areas is "A" and a total sum of the second areas is "B".

According to another aspect of the embodiment, an ultrasonic transducer includes a plurality of ultrasonic elements being arranged on the ultrasonic transducer with predetermined intervals. The plurality of ultrasonic elements include "m" first ultrasonic elements and "n" second ultrasonic elements. The "m" first ultrasonic elements include first diaphragms. The "m" first ultrasonic elements are configured and arranged to transmit and receive ultrasonic waves, where "m" represents the number of the first ultrasonic elements and is an integer of 1 or more. Each of the first diaphragms has a first area. The "n" second ultrasonic elements include second diaphragms. Each of the "n" second diaphragms has a second area being smaller than the first area. The "n" second ultrasonic elements are configured and arranged to transmit and receive the ultrasonic waves, where "n" representing the number of the second ultrasonic elements and is an integer larger than "m". The "m" first ultrasonic elements are electrically connected in series in a case where "m" is an integer of 2 or more. The "n" second ultrasonic elements are electrically connected in series. B/A is within a range of 0.9 to 1.1, when a total sum of the first areas is "A" and a total sum of the second areas is "B".

According to another aspect of the embodiment, an ultrasonic transducer includes a substrate, a supporting film, and a piezoelectric body. The substrate includes a plurality of openings. The supporting film is configured to cover the plurality of openings. The piezoelectric body is configured on the supporting film at one of the plurality of openings. The plurality of openings include "m" first openings, where "m" represents a number of the first openings and is an integer of 1 or more. Each of the first openings has a first opening area covered with the supporting film on a surface of the substrate. The plurality of openings include "n" second openings, where "n" represents a number of the second openings and is an integer larger than "m". Each of the second openings has a second opening area that is smaller than the first area. "m" first piezoelectric bodies, which are formed corresponding to the "m" first openings, of the piezoelectric body are electrically connected in series in a case where "m" is an integer of 2 or more. "n" second piezoelectric bodies, which are formed corresponding to the "n" second openings, of the piezoelectric body are electrically connected in series. B/A is within the range of 0.9 to 1.1, when a total sum of the first opening areas is "A" and a total sum of the second opening areas is "B".

According to another aspect of the embodiment, an ultrasonic transducer includes a substrate, a supporting film, and a piezoelectric body. The substrate includes a plurality of openings. The supporting film is configured to cover the plurality of openings. The piezoelectric body is configured on the supporting film at one of the plurality of openings. The plurality of openings include an arrangement opening group with predetermined intervals. The opening group include "m" first openings, where "m" represents a number of the first openings and is an integer of 1 or more. Each of the "m" first openings has a first opening area covered with the supporting film on a surface of the substrate. The opening group includes "n" second openings, where "n" represents a number of the second openings and is an integer larger than "m". Each of the "m" second openings has a second opening area that is smaller than the first area. "m" first piezoelectric bodies, which are formed corresponding to the "m" first openings, of the piezoelectric body are electrically connected in series in a case where "m" is an integer of 2 or more. "n" second piezoelectric bodies, which are formed corresponding to the "n" second openings, of the piezoelectric body are electrically connected in series. B/A is within the range of 0.9 to 1.1, when a total sum of the first areas is "A" and a total sum of the second areas is "B"

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic transducer comprising:
"m" first ultrasonic elements including first diaphragms, the "m" first ultrasonic elements being configured and arranged to transmit and receive ultrasonic waves, where "m" represents a number of the first ultrasonic elements and is an integer of 1 or more, each of the first diaphragms having a first area and a piezoelectric body that is disposed on the first area; and
"n" second ultrasonic elements including second diaphragms, each of the "n" second diaphragms having a second area and a piezoelectric body that is disposed on the second area, the second area being smaller than the first area, the "n" second ultrasonic elements being configured and arranged to transmit and receive the ultrasonic waves, where "n" represents a number of the second ultrasonic elements and is an integer larger than "m",
the "m" first ultrasonic elements being electrically connected in series by a first electric connection in a case where "m" is an integer of 2 or more,
the "n" second ultrasonic elements being electrically connected in series by a second electric connection, the second electric connection being electrically disconnected from the first electric connection,
B/A being within a range of 0.9 to 1.1, when a total sum of the first areas is "A" and a total sum of the second areas is "B".

2. The ultrasonic transducer according to claim 1, wherein "n" is an integer of 3 or more, and
in wiring to connect electrically each of the "n" second ultrasonic elements in series, a distance between two adjacent second ultrasonic elements among the "n" second ultrasonic elements is the same.

3. The ultrasonic transducer according to claim 1, wherein "m" is an integer of 3 or more,
"n" is an integer of 4 or more, and
in wiring to connect electrically each of the "m" first ultrasonic elements in series, a distance between two adjacent first ultrasonic elements among the "m" first ultrasonic elements is the same.

4. The ultrasonic transducer according to claim 3, wherein "k" is an integer of 4 or more, and
in wiring to connect electrically the "k" third ultrasonic elements in series, a distance between two adjacent third ultrasonic elements among the "k" third ultrasonic elements is the same.

5. The ultrasonic transducer according to claim 1 further comprising
"k" third ultrasonic elements including third diaphragms, each of the "k" third diaphragms having a third area being smaller than the second area, the "k" third ultrasonic elements being configured and arranged to transmit and receive the ultrasonic waves, where "k" represents a number of the third ultrasonic elements and is an integer larger than "m", wherein
the "k" third ultrasonic elements are electrically connected in series, and
C/A is within the range of 0.9 to 1.1, when a total sum of the third areas is "C".

6. The ultrasonic transducer according to claim 5, wherein "m" is an integer of 3 or more,
"n" is an integer of 4 or more,
"k" is an integer of 5 or more, and
all of the distance between two adjacent first ultrasonic elements among the "m" first ultrasonic elements, the distance between two adjacent second ultrasonic among the "n" second ultrasonic elements, and the distance between two adjacent third ultrasonic elements among the "k" third ultrasonic elements are the same.

7. An ultrasonic transducer comprising:
a plurality of ultrasonic elements being arranged on the ultrasonic transducer with predetermined intervals,
the plurality of ultrasonic elements including
"m" first ultrasonic elements including first diaphragms, the "m" first ultrasonic elements being configured and arranged to transmit and receive ultrasonic waves, where "m" representing the number of the first ultrasonic elements and is an integer of 1 or more, each of the first diaphragms having a first area and a piezoelectric body that is disposed on the first area, and
"n" second ultrasonic elements including second diaphragms, each of the "n" second diaphragms having a second area and a piezoelectric body that is disposed on the second area, the second area being smaller than the first area, the "n" second ultrasonic elements being configured and arranged to transmit and receive the ultrasonic waves, where "n" representing the number of the second ultrasonic elements and is an integer larger than "m",
the "m" first ultrasonic elements being electrically connected in series by a first electric connection in a case where "m" is an integer of 2 or more,
the "n" second ultrasonic elements being electrically connected in series by a second electric connection, the second electric connection being electrically disconnected from the first electric connection,
B/A being within a range of 0.9 to 1.1, when a total sum of the first areas is "A" and a total sum of the second areas is "B".

8. A probe comprising:
the ultrasonic transducer according to claim 1; and
a case in which the ultrasonic transducer is accommodated.

9. A diagnostic device comprising:
the ultrasonic transducer according to claim 1;
a case in which the ultrasonic transducer is accommodated; and
a device main body that is provided with a microcomputer configured to conduct a signal processing based on a signal output from the ultrasonic transducer.

10. An electronic instrument comprising:
the ultrasonic transducer according to claim 1;
a case in which the ultrasonic transducer is accommodated; and
a device main body that is provided with a microcomputer configured to conduct a signal processing based on a signal output from the ultrasonic transducer.

* * * * *